United States Patent
Billings

(10) Patent No.: US 10,075,046 B2
(45) Date of Patent: Sep. 11, 2018

(54) STEADY RATIO FOUR-BAR LINKAGE FOR GENUFLECTIVE ENERGY HARVESTING

(71) Applicant: Bionic Power Inc., Vancouver (CA)

(72) Inventor: John Scott Billings, Vancouver (CA)

(73) Assignee: Bionic Power Inc., Vancouver (CA)

( * ) Notice: Subject to any disclaimer, the term of this patent is extended or adjusted under 35 U.S.C. 154(b) by 554 days.

(21) Appl. No.: 14/882,855

(22) Filed: Oct. 14, 2015

(65) Prior Publication Data

US 2017/0110937 A1    Apr. 20, 2017

(51) Int. Cl.
*A61F 5/00* (2006.01)
*H02K 7/18* (2006.01)
*F03G 5/00* (2006.01)
*F03G 5/06* (2006.01)

(52) U.S. Cl.
CPC ............. *H02K 7/1861* (2013.01); *F03G 5/00* (2013.01); *F03G 5/06* (2013.01)

(58) Field of Classification Search
None
See application file for complete search history.

(56) References Cited

U.S. PATENT DOCUMENTS

| 3,901,223 A | 8/1975 | May |
| 3,969,773 A * | 7/1976 | Menschik ............... A61F 2/384 623/20.24 |
| 4,523,585 A * | 6/1985 | Lamb ..................... A61F 5/0123 602/16 |
| 5,020,790 A | 6/1991 | Beard et al. |
| 5,259,832 A * | 11/1993 | Townsend ............. A61F 5/0123 602/16 |
| 5,314,498 A | 5/1994 | Gramnas |
| 5,800,370 A | 9/1998 | Kubein-Meesenburg et al. |
| 9,622,899 B2 * | 4/2017 | Romo ................... A61F 5/0123 |
| 2005/0192523 A1 * | 9/2005 | Knecht ................. A61F 5/0123 602/26 |
| 2007/0010772 A1 * | 1/2007 | Ryan .................... A61F 5/0123 602/26 |
| 2009/0204038 A1 * | 8/2009 | Smith .................. A61F 5/0102 602/13 |
| 2013/0150761 A1 * | 6/2013 | Romo ...................... A61F 5/01 602/16 |

FOREIGN PATENT DOCUMENTS

| JP | 2007130459 | 5/2007 |
| WO | 2007016781 | 2/2007 |

OTHER PUBLICATIONS

Bionic Power Inc. "Bionic Power Powerwalk." Marketing Collateral, 2013.

(Continued)

*Primary Examiner* — Kim M Lewis
(74) *Attorney, Agent, or Firm* — Damien G. Loveland

(57) ABSTRACT

A mechanism has four connected links to mimic the motion of a knee joint. A lower link is oriented towards the vertical. A leverage ratio between flexion of the knee and relative angular displacement of certain links in the mechanism remains fairly steady over much of the range of motion of the mechanism. The mechanism may be used to drive an energy harvesting gearbox with steadier and more efficient energy harvesting at deep flexion, as well as with quieter operation.

20 Claims, 10 Drawing Sheets

(56) References Cited

OTHER PUBLICATIONS

Bionic Power Inc. "PowerWalk M-Series R5 Datasheet." retrieved on Oct. 14, 2015 from: http://bionic-power.com/downloads/PowerWalkMDatasheet%20V1.1.pdf.

Patent Cooperation Treaty International Search Report dated Jan. 17, 2017 issued for the parent application assigned International Application No. PCT/CA2016/051181 with an International Filing Date of Oct. 7, 2016.

Patent Cooperation Treaty International Written Opinion dated Jan. 17, 2017 issued for the parent application assigned International Application No. PCT/CA2016/051181 with an International Filing Date of Oct. 7, 2016.

* cited by examiner

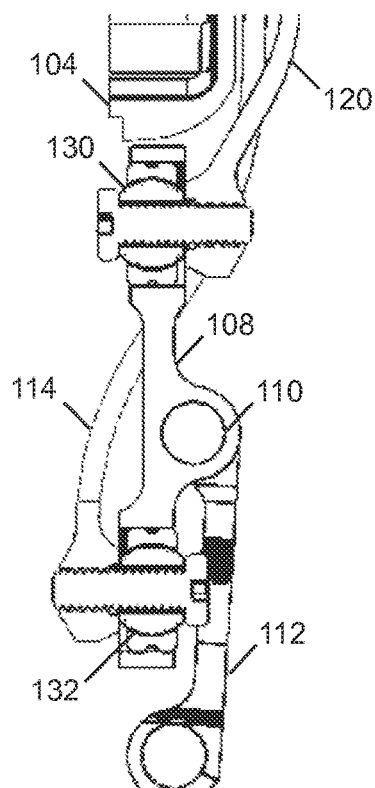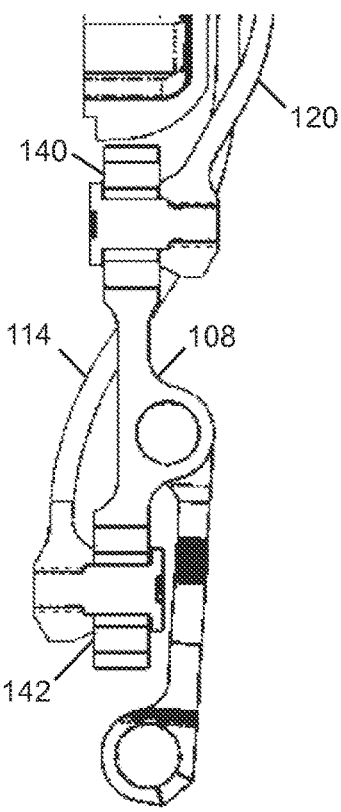
FIG. 8         FIG. 9
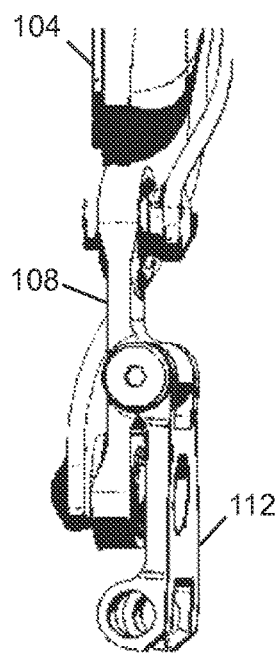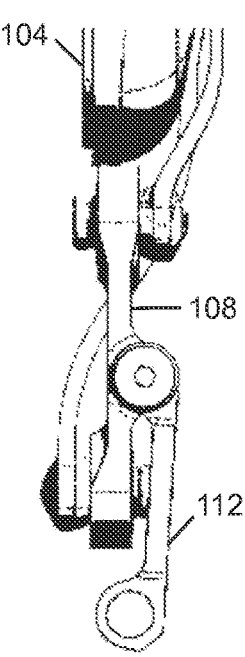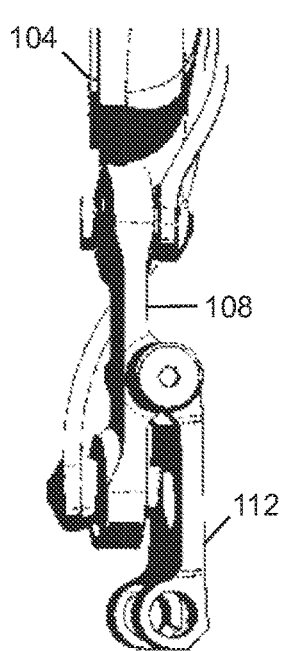
FIG. 10     FIG. 11     FIG. 12

STEADY RATIO FOUR-BAR LINKAGE FOR GENUFLECTIVE ENERGY HARVESTING

TECHNICAL FIELD

This application relates to energy harvesting from human body motion. More specifically, it relates to a four-bar linkage mechanism for harvesting energy from flexion and extension of a knee joint.

BACKGROUND

Energy may be harvested from the movement of body joints of humans and other animals by converting mechanical energy derived from such movement to electrical energy. Activities where body joints move repeatedly, such as walking, jogging, and running, for example, present opportunities to continually harvest energy from moving body joints. In some energy harvesting devices and methods, a generator driven by joint motion is coupled to an electrical load. Since the instantaneous mechanical power provided by body joints during repetitive or cyclical activities typically varies over the period of each cycle, both the electrical power supplied to the load and the forces applied to the body joint may be time-varying over each cycle. In some circumstances, the variations of delivered electrical power and/or forces applied to body joints that occur in this arrangement may be undesirable, for reasons such as efficiency and user comfort.

A knee joint 10 is shown in FIG. 1, in which a femur 12 and tibia 14 are depicted in an extended position. Also shown is a position of the knee joint where the femur has flexed to the right, to position 12A, as if the person were sitting down or squatting. The medial collateral ligament insertion 16 on the femur 12 is shown to move along arc 17 during flexion of the knee joint 10, the center of this ligament insertion passing through corresponding numbered points 1-6. Also, during flexion, the medial condyle 18 rolls and slides such that its geometrical center shifts, shown by corresponding numbered points 1-6 indicated by arrow 20. During extension and flexion the knee joint does not rotate on a fixed axis, but moves through both a rolling and sliding motion along the interface between the lower surface 22 of the femoral condyles and tibial plateau 24.

This means that a simple single pivot hinge does not provide a good approximation of knee kinematics. In the context of brace design, a single pivot system would result in migration of the brace as a result of the incongruent motion of the knee and the brace.

Tracking a point 20 at the approximate spherical center of the femoral condyles during extension and flexion results in an approximately straight line trajectory along the tibial plateau. This trajectory is referred to as femoral rollback. Being an approximate straight line trajectory, this has led knee brace and prosthetics designers to mimic this by implementing a Chebyshev four-bar linkage 29, shown schematically in FIG. 2. The linkage 29 has a lower link 30, two identical cross links 32, 34 and an upper link 36, all connected at their ends with pivot points 38. As the upper link 36 turns either to the left or the right, the constraining action of the cross links 32, 34 result in the center point 40 of the upper link moving in an approximately straight line 42. In order to achieve the approximate straight line trajectory, the three-way length ratio of the lower link 30 to cross link 32, 34 to upper link 36 must be 2:2.5:1. Conventionally, the lower link 30 is oriented horizontally.

FIG. 3 shows a knee joint with femur 12 and tibia 14, in which the femur would rotate to the right during flexion. A four-bar linkage 50 is superimposed on the joint. The side link 52 approximately aligns with the PCL (posterior cruciate ligament) 54, and can be referred to as the PCL link. The side link 56 approximately aligns with the ACL (anterior cruciate ligament) 58 and can be referred to as the ACL link. The crossing side links 52, 56 loosely resemble the ACL and PCL ligaments in both geometry and kinematic function. The upper link 57 connects to the upper ends of the ACL link 56 and the PCL link 52, and as it is in a fixed orientation relative to the femur, it may be called the femur link. The position of the lower link 59 is fixed relative to the tibia and angled downwards posteriorly, approximately parallel with the typical 10-15° incline of the tibial plateau. The lower link 59 may be called the tibia link.

Knee prosthetics use four-bar linkage mechanisms between a shin brace and a thigh brace, but these linkages have a gearing ratio that declines steeply as the knee is flexed. The angular velocity is low at deep flexion, and there is a high angular velocity at leg extension. This would lead to a sharp periodic peak in noise in an energy-harvesting gearbox.

This background information is provided to reveal information believed by the applicant to be of possible relevance to the present invention. No admission is necessarily intended, nor should be construed, that any of the preceding information constitutes prior art against the present invention.

SUMMARY OF INVENTION

The four-bar linkage of the present invention has a substantially steady ratio of knee flexion to angle between particular links. This results from the judicial choice of relative lengths of the four-bar linkage and the orientation of the tibia link of the linkage. The invention is useful for increased energy capture and smoother and quieter operation of genuflective energy harvesters that are positioned at the knee and which convert mechanical rotary input into electrical energy.

The geometry of the Chebyshev four-bar linkage (i.e. the lengths and starting orientations of each link relative to the position of the leg) has been varied to track the trajectory of the femoral condyles during flexion, while maintaining a near constant ratio between the angular displacement of the PCL link relative to the femur link and the angular displacement of the leg (i.e. flexion). The tibia link is oriented towards vertical. The result is improved deep flexion energy harvesting for a given mechanical-to-electrical system (i.e. a transduction system) and reduced noise at extension. A further result, compared to prior linkages, is the elimination of the need to sense crank angular position during gait for the energy harvesting algorithm, which means that a sensor can be eliminated and a simpler power algorithm used. The steady, or near constant, ratio also reduces the sensitivity to fit for differently shaped legs. Further still, the tracking point on the linkage is at the pivot of the PCL and femur links, allowing the gearbox to be positioned further up the leg for better human factors. The use of an elastomer bearing seat and/or a spherical bearing at two of the joints (i.e. pivots) in the four-bar linkage allows for an extra degree of rotational freedom along a virtual line between the joints. Alignment of this virtual line with the length of the tibia allows for accommodation of tibial rotation. The normal knee goes through approximately 20° of tibial rotation during flexion.

Disclosed herein is four-bar linkage comprising: a tibia link having first and second pivots; a femur link having third and fourth pivots; an ACL link connected to the first pivot and the third pivot; and a PCL link crossed over the ACL link and connected to the second and fourth pivots; wherein: the distance between third and fourth pivots is one unit; the distance between first and second pivots is between 1.3 and 1.6 units, to one decimal place; the distance between first and third pivots is between 2.0 and 2.8 units, to one decimal place; and the distance between second and fourth pivots is between 2.4 and 3.3 units, to one decimal place. The sum of the distance between third and fourth pivots and the distance between second and fourth pivots is equal to the sum of the distance between first and third pivots and the distance between first and second pivots, to within a tolerance of 0.2 units. In some embodiments, the tolerance may be 0.1 units.

Further disclosed herein is a four-bar linkage comprising: a tibia link having first and second pivots; a femur link having third and fourth pivots; an ACL link connected to the first pivot and the third pivot; and a PCL link crossed over the ACL link and connected to the second and fourth pivots; wherein: the distance between third and fourth pivots is one unit; the distance between first and second pivots is between 1.3 and 1.4 units to one decimal place; the distance between first and third pivots is between 2.0 and 2.1 units to one decimal place; and the distance between second and fourth pivots is 2.4 units to one decimal place. The sum of the distance between third and fourth pivots and the distance between second and fourth pivots is equal to the sum of the distance between first and third pivots and the distance between first and second pivots, to within a tolerance of 0.1 units.

Still further disclosed herein is a four-bar linkage comprising: a tibia link having first and second pivots; a femur link having third and fourth pivots; an ACL link connected to the first pivot and the third pivot; and a PCL link crossed over the ACL link and connected to the second and fourth pivots; wherein: the distance between third and fourth pivots is one unit; the distance between first and second pivots is between 1.3 and 1.4 units to one decimal place; the distance between first and third pivots is between 2.0 and 2.1 units to one decimal place; and the distance between second and fourth pivots is 2.4 units to one decimal place. The sum of the distance between third and fourth pivots and the distance between second and fourth pivots is substantially equal to the sum of the distance between first and third pivots and the distance between first and second pivots.

The four-bar linkage may be included in a knee-mounted energy harvester, wherein: a straight line between the first and second pivots is oriented leaning at 15°±5° forwards from a vertical direction when a wearer of the harvester is standing upright with said knee extended; a further straight line between the third and fourth pivots is oriented leaning at 20°±5° rearwards from said vertical direction; the tibia link is connected to the ACL and PCL links via joints that permit the tibia link to twist about an axis between first and second pivots; and an angular displacement of the femur link relative to the PCL link divided by an angular displacement of the femur link relative to the tibia link yields a leverage ratio that is steady to within about 20% over a range of about −15° to about 150° of flexion of said knee.

BRIEF DESCRIPTION OF DRAWINGS

The following drawings illustrate embodiments of the invention, which should not be construed as restricting the scope of the invention in any way.

FIG. 8 is a cross sectional view of the lower portion of the four-bar linkage in which the tibia link is connected via spherical bearings to the ACL and PCL links.

FIG. 9 is a cross sectional view of the lower portion of the four-bar linkage in which the lower link is connected via elastomeric cups to the ACL and PCL links.

FIGS. 10-12 show twisting motion of the lower portion of the four-bar linkage according to an embodiment of the present invention.

DESCRIPTION

A. Glossary

ACL, or anterior cruciate ligament—one of a pair of crossed ligaments that join the tibia to the femur. The ACL is connected to the anterior of the tibia and forms a cross with the PCL.

Femoral condyle—one of the two round prominences at the lower end of a femur. The inner condyle is the medial condyle and the outer one the lateral condyle.

Femoral rollback—The backwards trajectory of the center of the femoral condyles during flexion of the knee. This is synonymously referred to as either the GCA (Geometric Center Axis) or the FFC (Facet Flexion Centers).

Femur—the thigh bone.

Flexion—the angle through which the knee bends, where 0° represents an extended knee and about 150° represents a squatting orientation.

Hyperextension—an excessive joint movement in which the joint is straightened beyond its normal position.

PCL, or posterior cruciate ligament—one of a pair of crossed ligaments that join the tibia to the femur. The PCL is connected to the posterior of the tibia, and forms a cross with the ACL.

Tibia—the shin bone.

Tibial rotation—the twisting of the tibia about its axis that occurs as the knee is extended and flexed. The normal knee goes through approximately 20° of tibial rotation during flexion.

B. Industrial Applicability

The four-bar linkage of the present invention is useful for improved genuflective energy harvesters, in which the ratio of knee flexion to driven angle in a gearbox is substantially constant, resulting in increased energy capture at deep flexion and smoother and quieter operation.

C. Exemplary Embodiment

Figure 1:
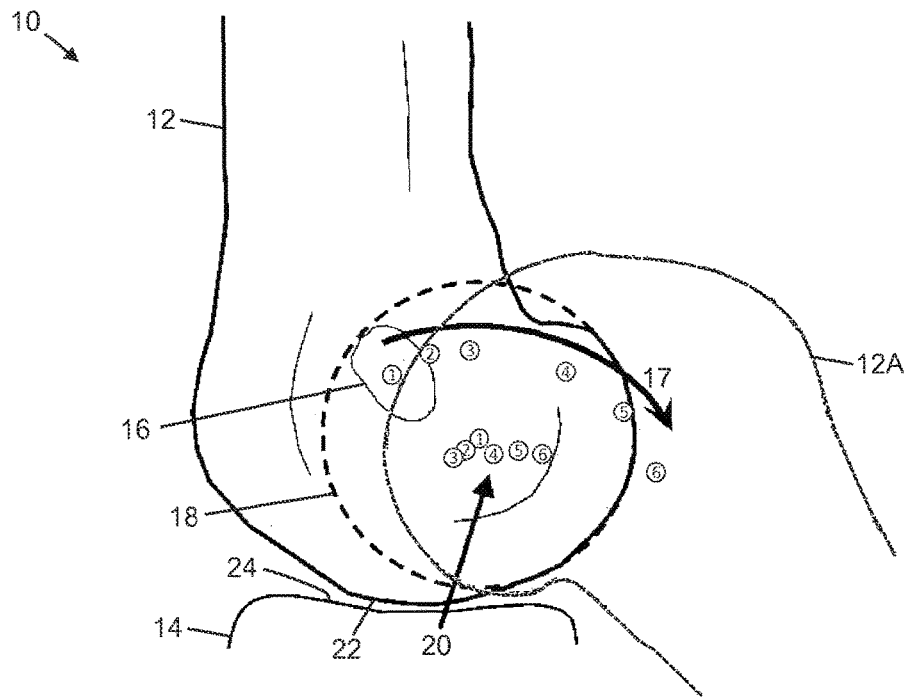
FIG. 1 is a prior art schematic diagram of a knee joint in extended and flexed positions.
Figure 2:
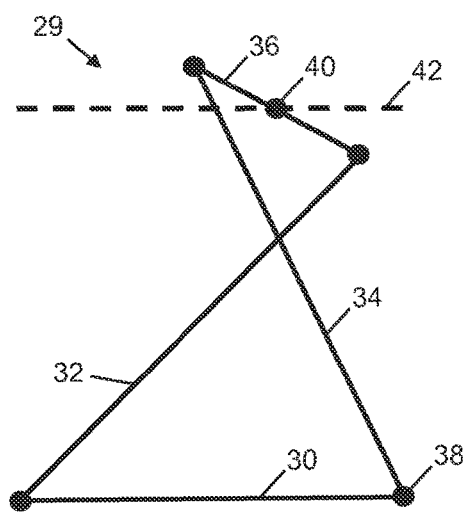
FIG. 2 is a prior art diagram of a Chebyshev four-bar linkage.
Figure 3:
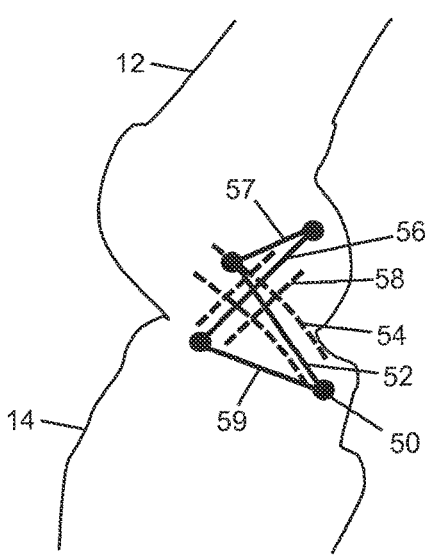
FIG. 3 is a prior art four-bar linkage superimposed on a knee joint.
Figure 4:
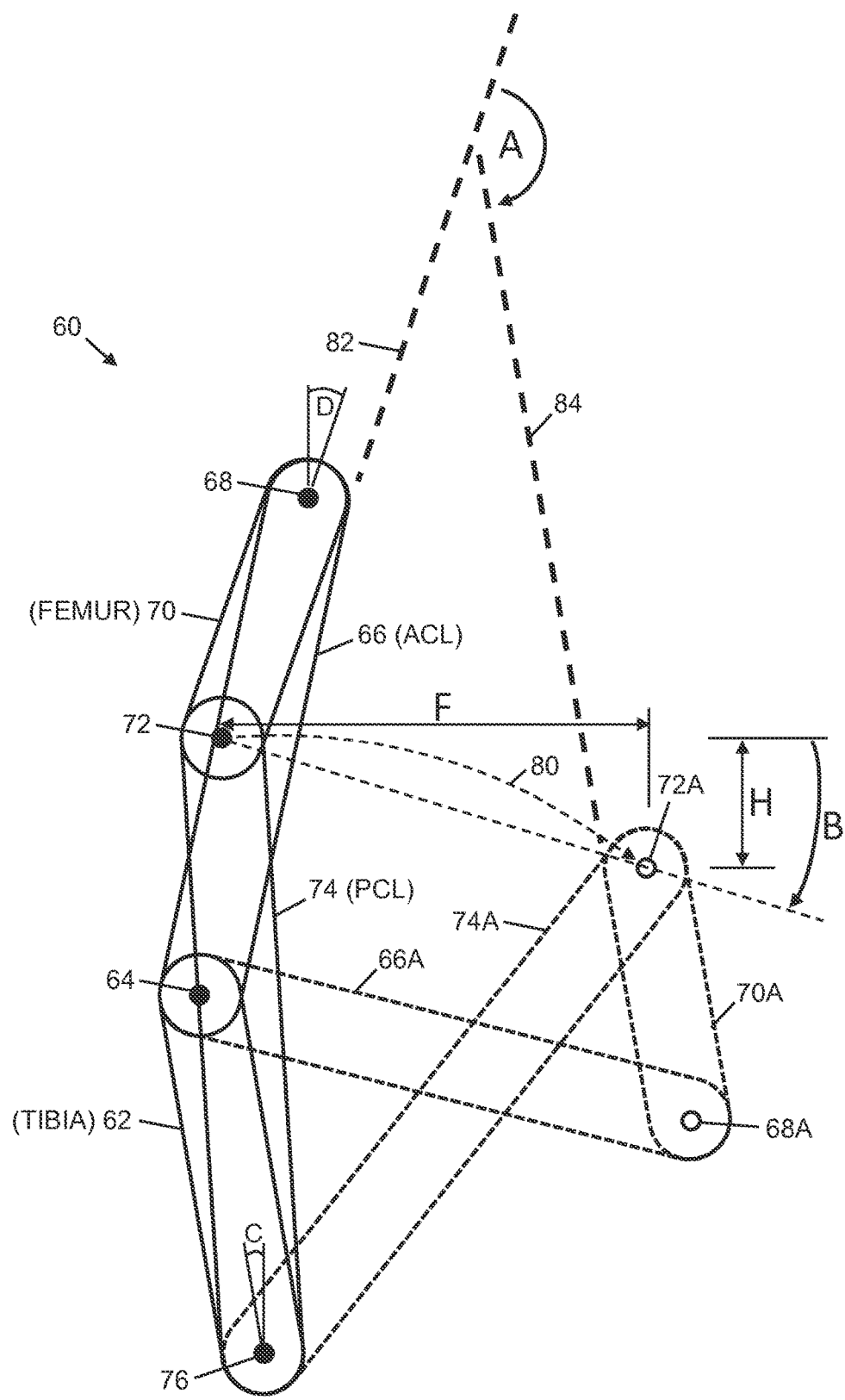
FIG. 4 is a schematic representation of a four-bar linkage according to an embodiment of the present invention.

Referring to FIG. 4, a four-bar linkage 60 according to an exemplary embodiment of the present invention is shown. The linkage 60 is shown, in solid lines, in approximately the orientation in which it would appear when fitted to an energy harvesting knee brace worn by human in the standing position. This linkage 60 as shown would be fitted to the outside of a wearer's left knee joint, and as such, the upper portion of the linkage would move to the right as the knee is flexed, assuming that the tibia remains stationary. As it can be seen, the lower link, or tibia link 62, is oriented more in a vertical position (i.e. at <45° to the vertical) than in a horizontal position (i.e. at >45° to the vertical). In some embodiments, the tibia link is oriented between 10°±5° and 25°±5° to the vertical. The tibia link 62 is in a fixed orientation relative to the tibia, mounted at angle C forward from the vertical when the wearer of the harvesting device is standing upright with an extended knee joint.

The tibia link 62 is connected via pivot 64 to the ACL link 66, which in turn is connected via pivot 68 to the femur link 70. The lower end of the femur link 70 is connected by pivot 72 to the PCL link 74, which in turn is connected to the tibia link 62 by pivot 76.

As the knee is flexed, where, for the purposes of FIG. 4, the tibia remains stationary and the femur moves to the right, the femur link 70 moves to the right and rotates in a clockwise fashion, to position 70A, so that it is almost inverted compared to its original position. The PCL link 74 moves to position 74A during flexion, and the ACL link 66 moves to position 66A. Pivot point 68 between the femur link 70 and the PCL link 74 moves to position 68A.

As flexion occurs, the lower pivot 72 of the femur link 70 moves along an arc 80 to position 72A. Note that the final position 72A of the lower pivot 72 after the knee has flexed is a distance H below where it was in its original position, when the knee was extended. This downwards displacement of the pivot 72 approximates to movement along a path that is inclined an angle B below the horizontal. This path may be considered to approximate the incline of the tibial plateau. Distance F measured along the horizontal is the horizontal displacement of the pivot 72 during flexion. For lesser flexions than shown here, the angle B will be lower, and the distance H will also be less.

The angle that the femur moves through is the same as the angle that the femur link 70 moves through. This angle is shown by angle A between dotted line 82 extending from the femur link 70 in its extended position and dotted line 84 extending from the femur link 70A when the knee is flexed.

In this example, the angle of flexion A is about 150°, corresponding to a typical full squat, and the angle B is about 17°. If the flexion angle A were only 60°, which may be typical of a normal gait on flat ground, then angle B would be about 5°.

For a non-limiting example, the tibia link may measure 33 mm from pivot 76 to pivot 64; the ACL link 66 may measure 46 mm from pivot 64 to pivot 68; the PCL link 74 may measure 56 mm from pivot 72 to pivot 76; and the femur link 70 may measure 23 mm from pivot 68 to pivot 72. Distance F is about 40 mm, and distance H is 12 mm. The angle C of the tibia link 62 is 10° leaning forwards relative to the wearer. The angle D of the femur link 70 is 20° leaning rearward from vertical relative to the wearer. These dimensions may be changed depending on the size of the person to which an energy harvesting device is to be fitted. The ratio of the inter-pivot lengths of the links 62, 66, 74, 70 is, in this example, is approximately 1.4:2:2.4:1, corresponding to TIBIA:ACL:PCL:FEMUR. In order to maintain the functionality of this embodiment as the sizes of the links 62, 66, 74, 70 are changed, the ratio between the lengths given above should be maintained.

For another non-limiting example, the tibia link may measure 27 mm from pivot 76 to pivot 64; the ACL link 66 may measure 44 mm from pivot 64 to pivot 68; the PCL link 74 may measure 50 mm from pivot 72 to pivot 76; and the femur link 70 may measure 21 mm from pivot 68 to pivot 72. The ratio of the inter-pivot lengths of the links 62, 66, 74, 70 is, in this example, is approximately 1.3:2.1:2.4:1, corresponding to TIBIA:ACL:PCL:FEMUR.

Besides the four-bar linkage being defined by a ratio as given above, for example, the inter-pivot lengths of the links should satisfy the following equation, to within an acceptable tolerance:

$$\text{FEMUR} + \text{PCL} = \text{ACL} + \text{TIBIA}$$

With regards to the two ratios given above, in both cases, both sides of the equation add up to 3.4. The equation may alternatively be expressed as a range, where the inter-pivot length of the femur link is 1 unit:

$$(\text{FEMUR} + \text{PCL}) - (\text{ACL} + \text{TIBIA}) = 0 \pm 0.1 \text{ units}$$

If the above condition is not satisfied, the steady ratio becomes broken at full extension, such that the curve increases or decreases rapidly. For example, if the difference between (FEMUR+PCL) and (ACL+TIBIA) is more than 0.2 units, the ratio is significantly affected at full extension and the linkage becomes much more sensitive to fit on the wearers' legs (i.e. how the linkage should 'start' on each wearer at their 0° flexion point).

The relative angular motion between the PCL link 74 and the femur link 70, at pivot point 72, may be used to provide power to a gearbox of an energy harvester. Pivot point 72 may therefore correspond to a drive axis of the gearbox. Also, the pivot point 72 may be aligned with the center of the femoral condyle, which means that a condyle pad worn by the wearer of an energy harvester may be centered on the pivot 72. This will greatly benefit condyle pad simplicity and form factor.

While the links 62, 66, 70, 74 of the four-bar linkage 60 have been shown to be flat, or in the same plane allowing for overlap, it is possible that one or more of the linkages may be bent out of the plane. If this is so, then the axes of the pivot points 64, 68, 72, 76 should be parallel, and spaced according to FIG. 5, for example, when viewed from the ends of the axes.

Figure 5:
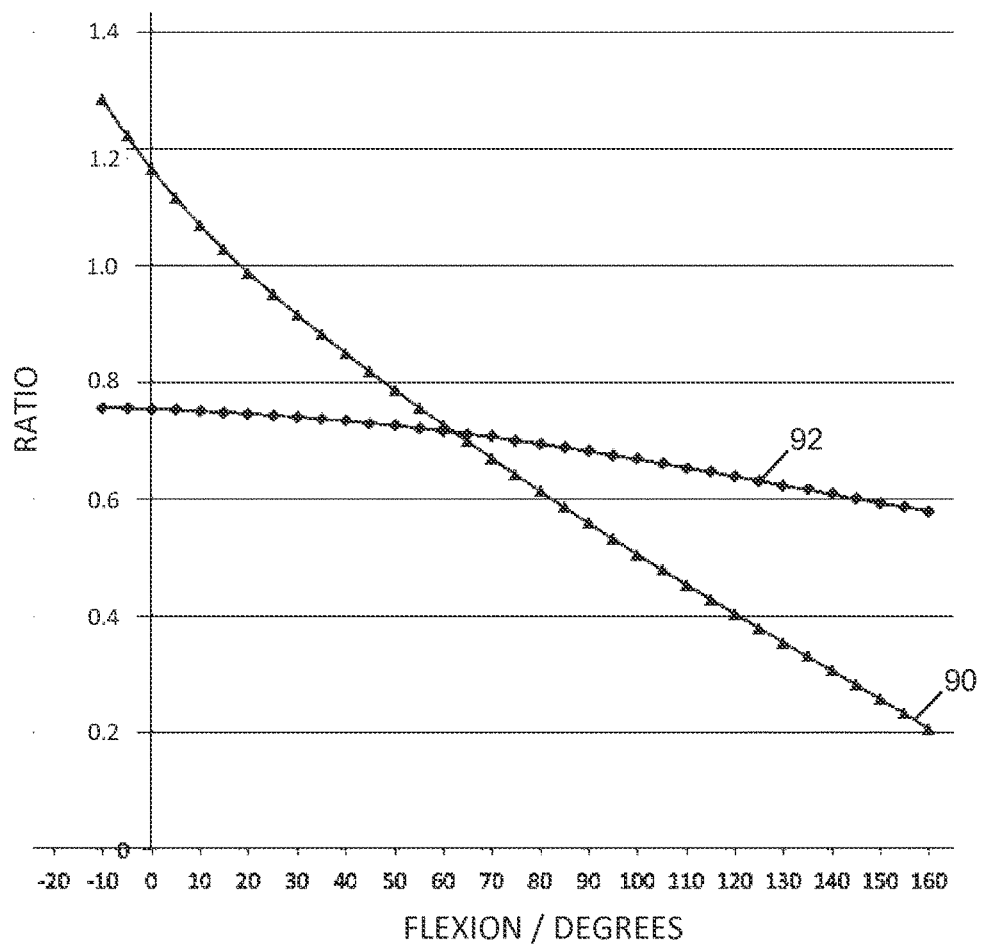
FIG. 5 is a graph showing the variation of the leverage ratio with flexion angle, for both an embodiment of the present invention and a prior art four-bar linkage.

Referring to FIG. 5, a graph is shown of the leverage ratio (y-axis) of a four-bar linkage as a function of knee flexion angle (x-axis). The leverage ratio is the change in angle between the femur link 70 and the PCL link 74, divided by the angle the knee bends through as it flexes. The leverage ratio is shown for a prior art four-bar linkage 90, in which the leverage ratio varies by about a factor of four as the flexion angle varies from 0° to 150°, i.e. from about 1.2 to 0.3. The leverage ratio of the four-bar linkage of the present invention is also shown by line 92. It can be clearly seen that the ratio is much more constant for the four-bar linkage of the present invention, declining by about only 20% over the same range. Generally speaking this decline directly affects deep flexion power generation. Thus it should be minimized for increased overall energy harvesting and it may be expected that any decline of 25% or less, for example, would be acceptable. More importantly, the decline is only about 7% over the flexion range of 60° typical for a normal, flat-ground gait. As such, the leverage ratio of the four-bar linkage mechanism disclosed herein is reasonably steady when compared to the leverage ratio of prior art mechanisms. In one embodiment, an angular displacement of the femur link relative to the PCL link divided by an angular displacement of the femur link relative to the tibia link yields a leverage ratio that is steady to within about 20% over a range of 165° of angular displacement of the femur link relative to the tibia link. During gait, the leg accelerates and decelerates and applies a range of torque. The four-bar linkage transmits leg movement to and from the gearbox. The near-constant leverage ratio eliminates the need for another level of variation in the linkage on top of the biomechanical variable. The linkage allows the gearbox to 'see' directly what the leg is doing but through a more or less constant 80% 'lens', rather than through a linkage that itself imparts significant variation to what the leg is doing. In addition, the near-constant leverage ratio provides a more optimal angular velocity profile for operation around the generator's speed constant. In other embodiments having a slightly different ratio of the links, the decline in leverage ratio for a 0° to 60° flexion may be from 0.8 to 0.75, which is about a 6% decline.

Figure 7:
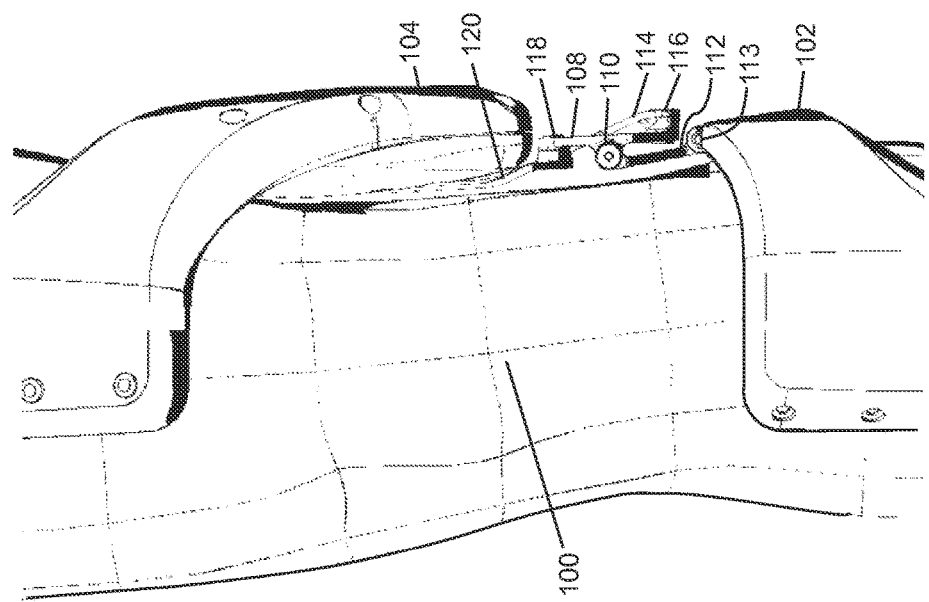
FIG. 7 is a front view of the knee and brace of FIG. 6.
Figure 6:
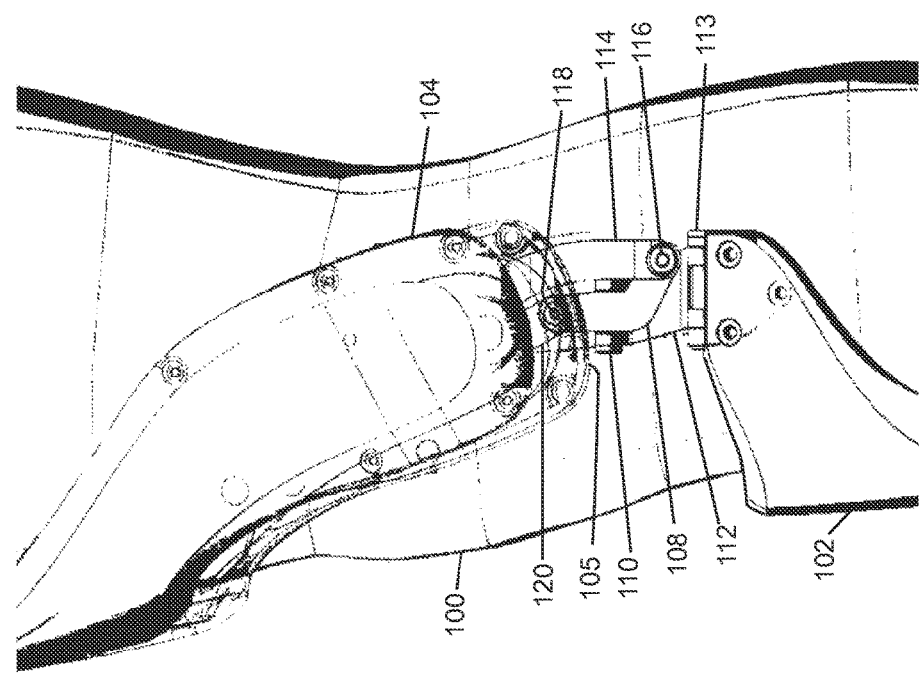
FIG. 6 is an outer-side view of a left knee fitted with an energy harvesting brace according to an embodiment of the present invention.

Referring to FIGS. 6 and 7 together, an energy harvester employing the four-bar linkage is shown on the outer side of a wearer's left knee 100. FIG. 6 shows a side view, and FIG. 7 shows a front view. As well as the four-bar linkage, the energy harvester includes a lower, shin brace 102 strapped around the wearer's lower leg and an upper, thigh brace 104 is strapped around the wearer's upper leg. The thigh brace 104 houses a gearbox and generator for converting mechanical motion of the four-bar linkage to electrical energy. For comparison, the position of a prior art thigh brace 105 is also shown, which extends lower than the thigh brace 104 for the current invention. The extent to which the upper thigh braces 104, 105 descend is governed by the need to enclose at least a tracking point, or driving pivot of the four-bar linkage. It is preferable if the upper thigh brace terminates higher up the leg rather than lower, in order to reduce the extent to which the lower end of the thigh brace projects beyond the front of the knee when squatting. Unexpectedly, the enclosed driving pivot 72 (not visible in FIG. 6) of the invented four-bar linkage is higher up than in prior linkages, allowing the thigh brace 104 to terminate higher up than prior thigh braces 105. In prior linkages, the tracking point would be at the center of the femur link.

The tibia link 108 is connected at a central point 110, which is a pivot additional to the pivots of the four-bar linkage, to a connector 112, which in turn is connected by additional pivot 113 to the shin brace 102. The additional pivots 110, 113 permit the shin brace to move inwards and outwards from the side of the leg, relative to the thigh brace, in order to allow the same harvester to fit to different leg shapes, including different levels of varus and valgus deformities (i.e. bow-legged and knock-kneed respectively). The additional pivots also accommodate a normal movement of varus/valgus during normal flexion (which is about 5°). Such movement does not affect the almost vertical orientation of the tibia link 108 in relation to its being part of a four-bar linkage. Note also that the shape of the tibia link 108 does not need to be linear; it is only the distance between the pivots 116, 118 that define the tibia link. The lower portion of the PCL link 114 is visible and shown connected to pivot point 116. The lower portion of the ACL link 120 is shown connected to the pivot point 118. The upper portion of the ACL link 120, the upper portion of the PCL link 114, and the femur link are hidden by the casing of the thigh brace 104.

FIG. 8 shows the lower portion of the four-bar linkage, showing how the tibia link 108 is attached via spherical bearings 130, 132 to the ACL link 120 and the PCL link 114 respectively. It can be seen that the ACL link 120 and PCL link 114 do not necessarily need to be flat, nor lie completely in the same plane as the tibia link 108. This is true of all the links in the four-bar linkage mechanism, and their form factors may be selected to wrap around other features in the energy harvester. In order for the energy harvester to be compact, the ACL link 120 and PCL link 114 curve behind the lower portion of the thigh brace 104, which houses the gearbox. Also shown is the additional pivot 110, via which the tibia link 108 is attached to the connector 112 that connects to the shin brace. The spherical joints 130, 132 allow the tibia link 108 to twist about its axis without being constrained by the remainder of the four-bar linkage, namely the ACL link 120 and the PCL link 114. This allows for some twisting movement between the thigh brace 104 and the shin brace 102, to allow for different leg shapes and adjustments to the wear position, as well as for tibial rotation that naturally occurs during gait. The spherical joints 130, 132 allow for free, unsprung twisting motion.

Other articulated joints may be used to connect the tibia link to the other links. For example, FIG. 9 shows an alternate embodiment in which the tibia link 108 is attached to the ACL link 120 and PCL link 114 with polyurethane cups 140, 142 respectively. These also allow the tibia link 108 to twist along its axis, but provide a spring force to return the tibia link back to its central position. In other embodiments, other elastomers may be used to provide the spring effect.

FIGS. 10-12 show the twisting motion of the tibia link 108 relative to the thigh brace 104 and the remainder of the four-bar linkage. In FIG. 10, the tibia link 108 and connector 112 are twisted about 10° to the left. In FIG. 11, the tibia link and connector 112 are in their central position. In FIG. 12, the tibia link 108 and connector 112 are twisted about 10° to the right.

Figure 15:
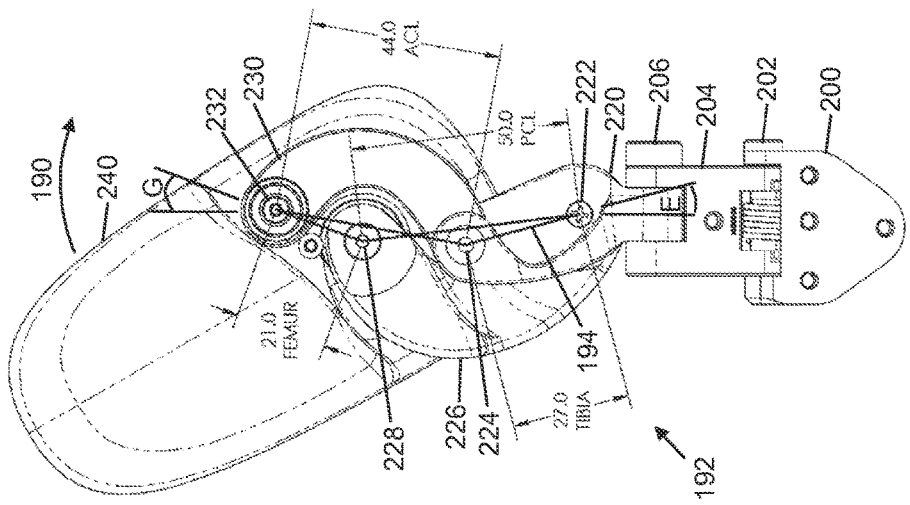
FIGS. 13-15 show different views of a gearbox cover, four-bar linkage and lower connector according to an embodiment of the present invention.
Figure 14:
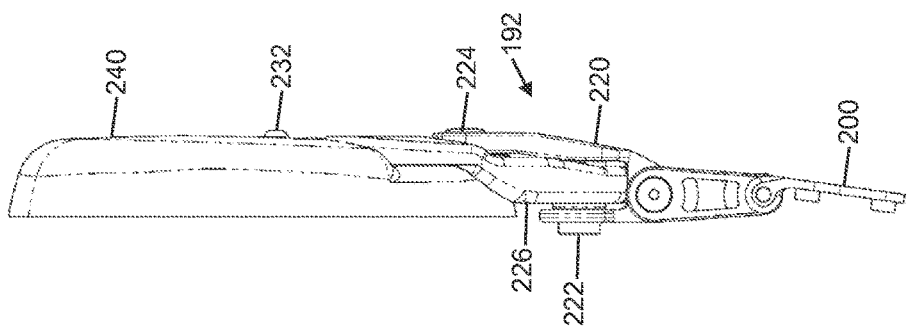
Figure 13:
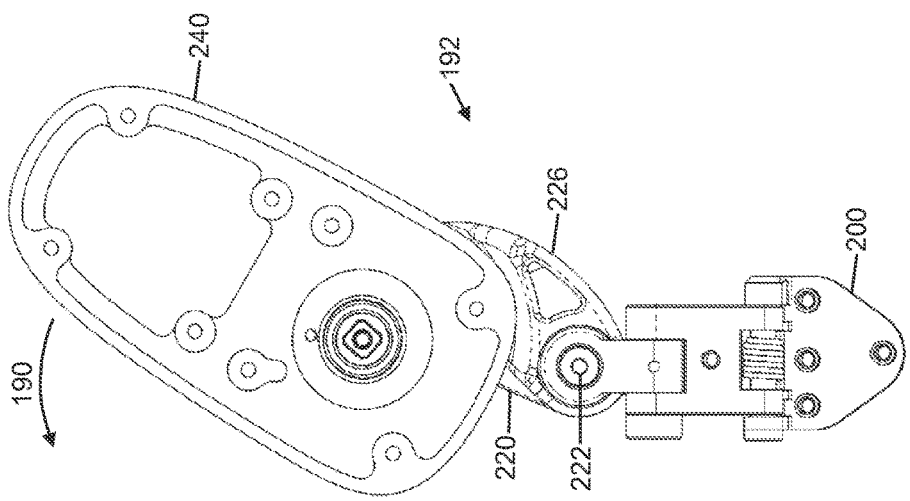

Referring to FIGS. 13-15 together, different views of an embodiment of the four-bar linkage 192 at 0° flexion are shown. Arrows 193 indicate the direction in which the femur moves relative to the here stationary tibia when the knee is flexing. A skeleton four-bar linkage 194 is superimposed on FIG. 15. Bracket 200 attaches to a shin brace (not shown) and, via pin 202, the bracket is shown attached to the lower end of connector 204. Pin 206 connects the connector 204 to the tibia link 220. The tibia link 220 has lower pivot 222 and upper pivot 224. The tibia link 220 is connected via pivot 222 to PCL link 226. The PCL link 226 is connected via pivot 228 to the gearbox housing 240, which is attached and/or housed in the thigh brace (not shown). The ACL link 230 is attached by pivot 232 to the gearbox housing 240. The femur link is defined by the locations of the pivots 228, 232 in the gearbox housing 240. Pivot 228 is the driving point. The tibia link 220, the PCL link 226 and the ACL link 230 have generally wide, flattened and curved forms in order to reduce the appearance of gaps that might cause scissor-like pinch points as the four-bar linkage moves. Avoiding pinch points is important in order to reduce the likelihood of injury to the wearer, trapping of clothing and damage to the linkage. In one embodiment, the tibia link, the ACL link and the PCL link have flat, curved shapes and an overlapping configuration such that pinch points between any two of said links are reduced over a range of 165° of angular displacement of the femur link relative to the tibia link, compared to if the tibia, ACL and PCL links had rectilinear shapes.

In FIG. 15, exemplary dimensions of the links of the four-bar linkage are given. For example, the tibia link 220 may measure 27 mm from pivot 222 to pivot 224; the ACL link 230 may measure 44 mm from pivot 224 to pivot 232; the PCL link 226 may measure 50 mm from pivot 222 to pivot 228; and the femur link as defined by the gearbox housing 240 may measure 21 mm between pivots 228 and 232. As such the ratio of the links is given approximately by TIBIA:ACL:PCL:FEMUR=1.3:2.1:2.4:1. The pivots 222, 224 of the tibia link are aligned at an angle E of 15° to the vertical, leaning forwards relative to the wearer. The pivots 228, 232 of the femur link are aligned at an angle G of 20° to the vertical, leaning rearwards from the wearer. In the four-bar linkage 192 of FIGS. 13-15, the angular displacement of the femur link relative to the tibia link is possible over a range from about −15° to about 200°, where 0° corresponds to an extended position of a knee joint.

Figure 16:
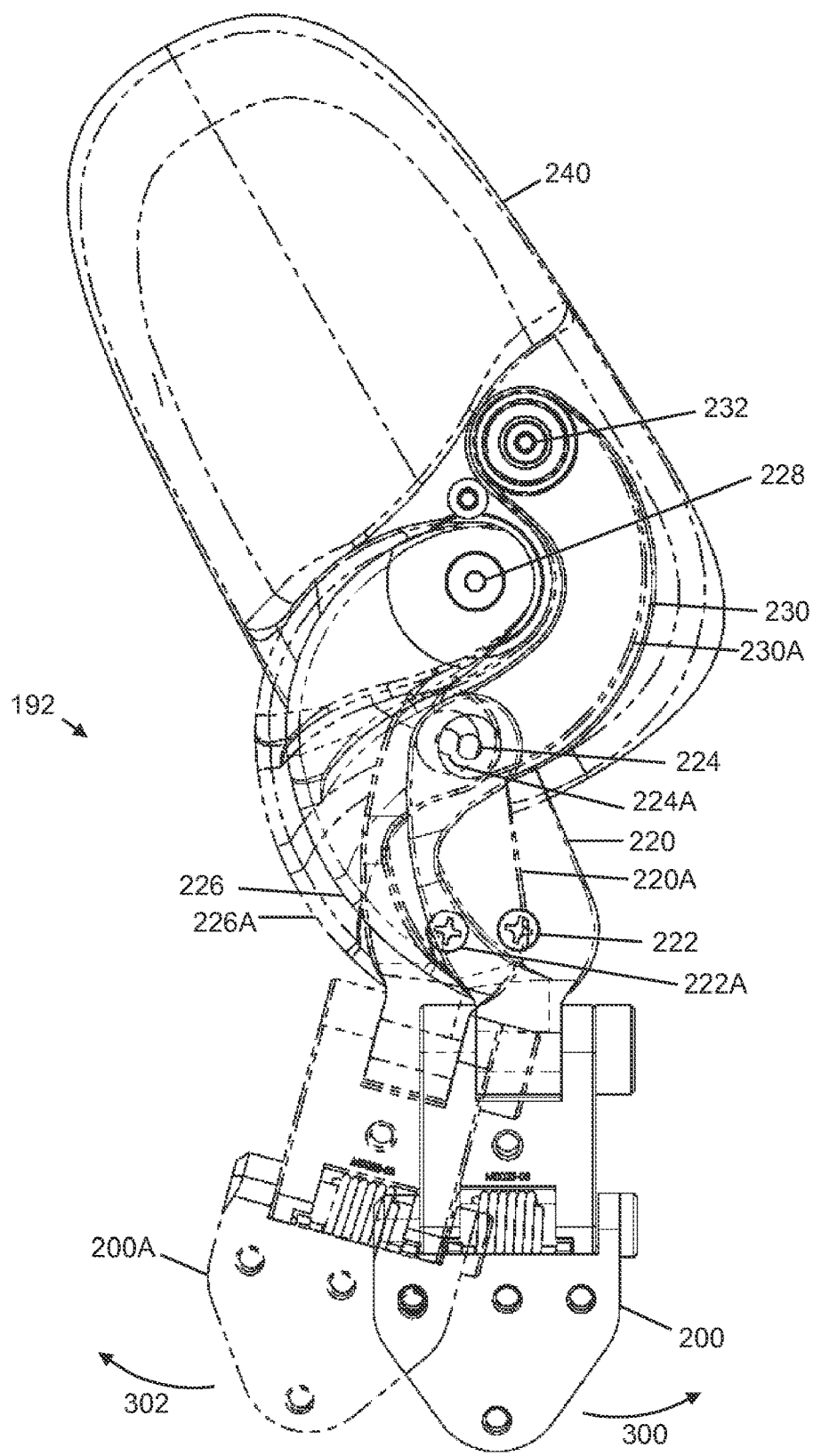
FIG. 16 shows a gearbox cover, four-bar linkage and lower connector in extended and hyperextended positions, according to an embodiment of the present invention.

Referring to FIG. 16, the four-bar linkage 192 of FIGS. 13-15 is shown at 0° flexion and −15° flexion, which corresponds to hyperextension of the knee joint. Arrow 300 shows the motion of the tibia relative to the femur when normally flexing the knee. Arrow 302 shows the motion of the tibia relative to the femur when hyperextending the knee. During flexion from 0° to −15° the bracket 200 moves to position 200A; the tibia link 220 moves to position 220A; the lower tibia pivot 222 moves to position 222A; the upper tibia pivot 224 move to position 224A; the PCL link 226 moves to position 226A; and the ACL link 230 moves to position 230A. The femur pivots 228, 232 remain stationary relative to the gearbox housing 240.

Figure 17:
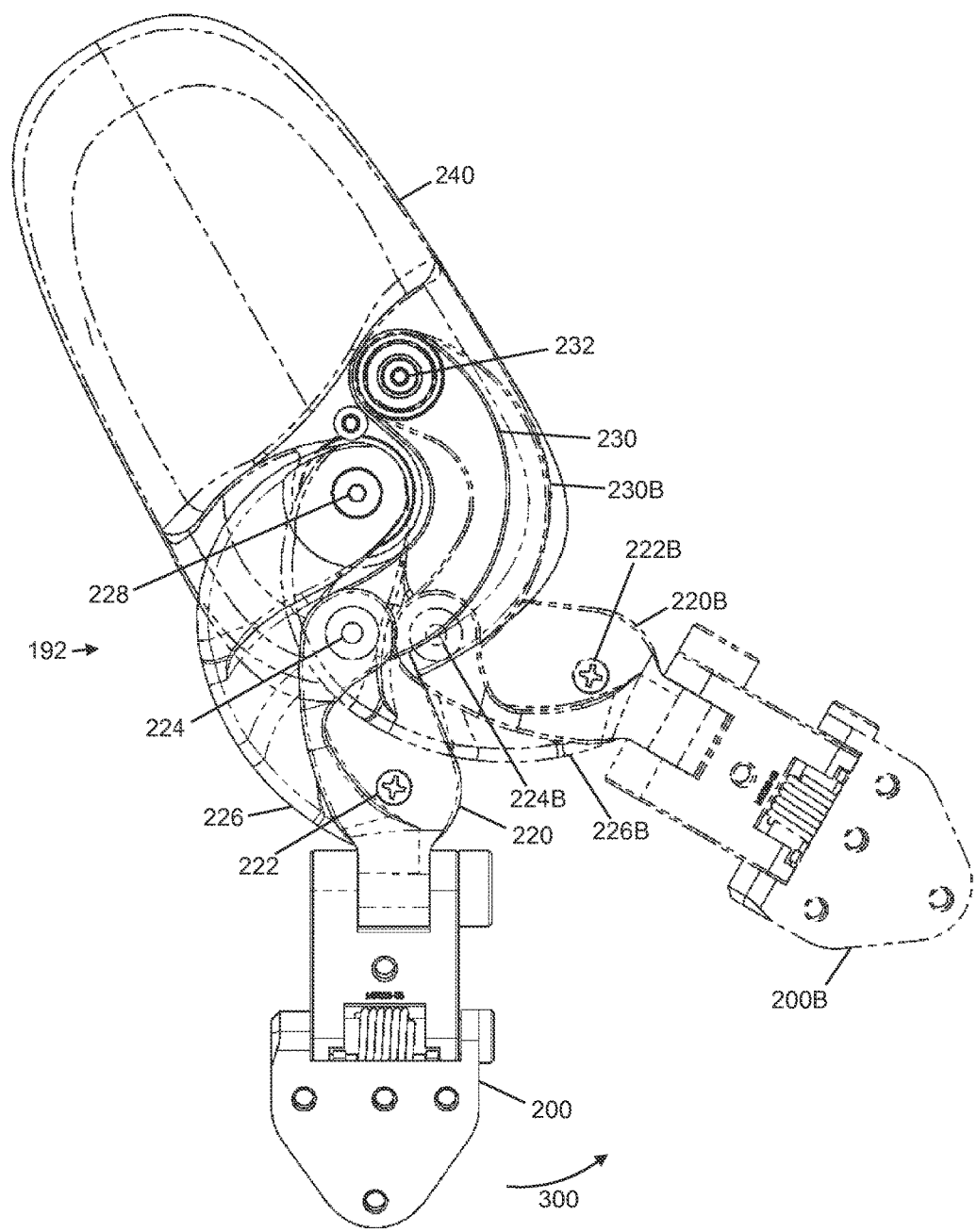
FIG. 17 shows a gearbox cover, four-bar linkage and lower connector in extended and 60° flexed positions, according to an embodiment of the present invention.

Referring to FIG. 17, the four-bar linkage 192 of FIGS. 13-15 is shown at 0° flexion and 60° flexion. Arrow 300 shows the motion of the tibia relative to the femur when normally flexing the knee. During flexion from 0° to 60° the bracket 200 moves to position 200B; the tibia link 220 moves to position 220B; the lower tibia pivot 222 moves to position 222B; the upper tibia pivot 224 move to position 224B; the PCL link 226 moves to position 226B; and the ACL link 230 moves to position 230B. The femur pivots 228, 232 remain stationary relative to the gearbox housing 240.

Figure 18:
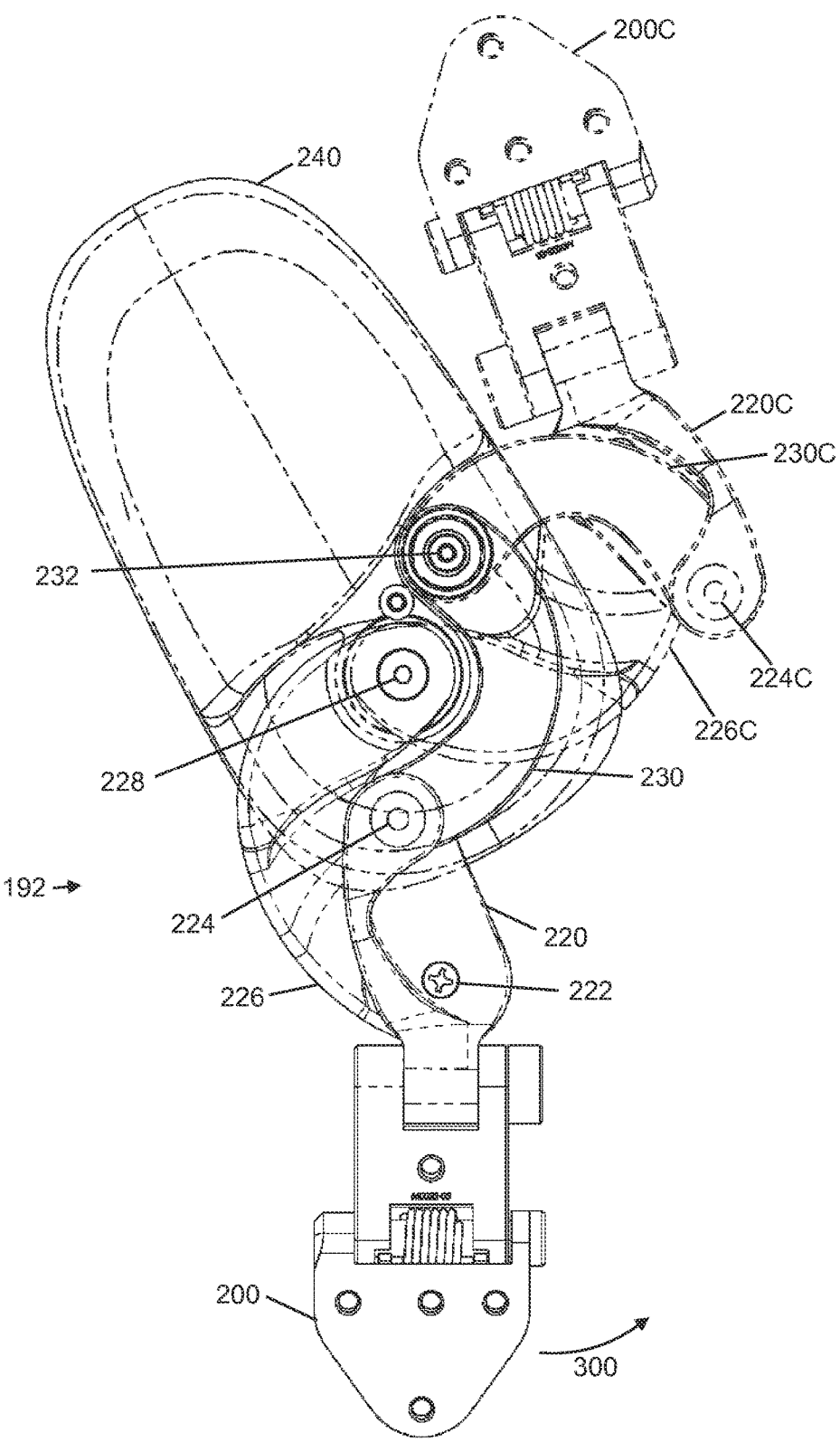
FIG. 18 shows a gearbox cover, four-bar linkage and lower connector in extended and 200° flexed positions, according to an embodiment of the present invention.

Referring to FIG. 18, the four-bar linkage 192 of FIGS. 13-15 is shown at 0° flexion and 200° flexion, which corresponds to a position in which the device may be packed compactly for shipping, for example. Arrow 300 shows the motion of the tibia relative to the femur when normally flexing the knee, which is the same direction in which the bracket 200 is moved for packing. During flexion from 0° to 200° the bracket 200 moves to position 200C; the tibia link 220 moves to position 220C; the lower tibia pivot 222 moves to a hidden position behind the ACL link 230C; the upper tibia pivot 224 move to position 224C; the PCL link 226 moves to position 226C; and the ACL link 230 moves to position 230C. The femur pivots 228, 232 remain stationary relative to the gearbox housing 240.

Figure 19:
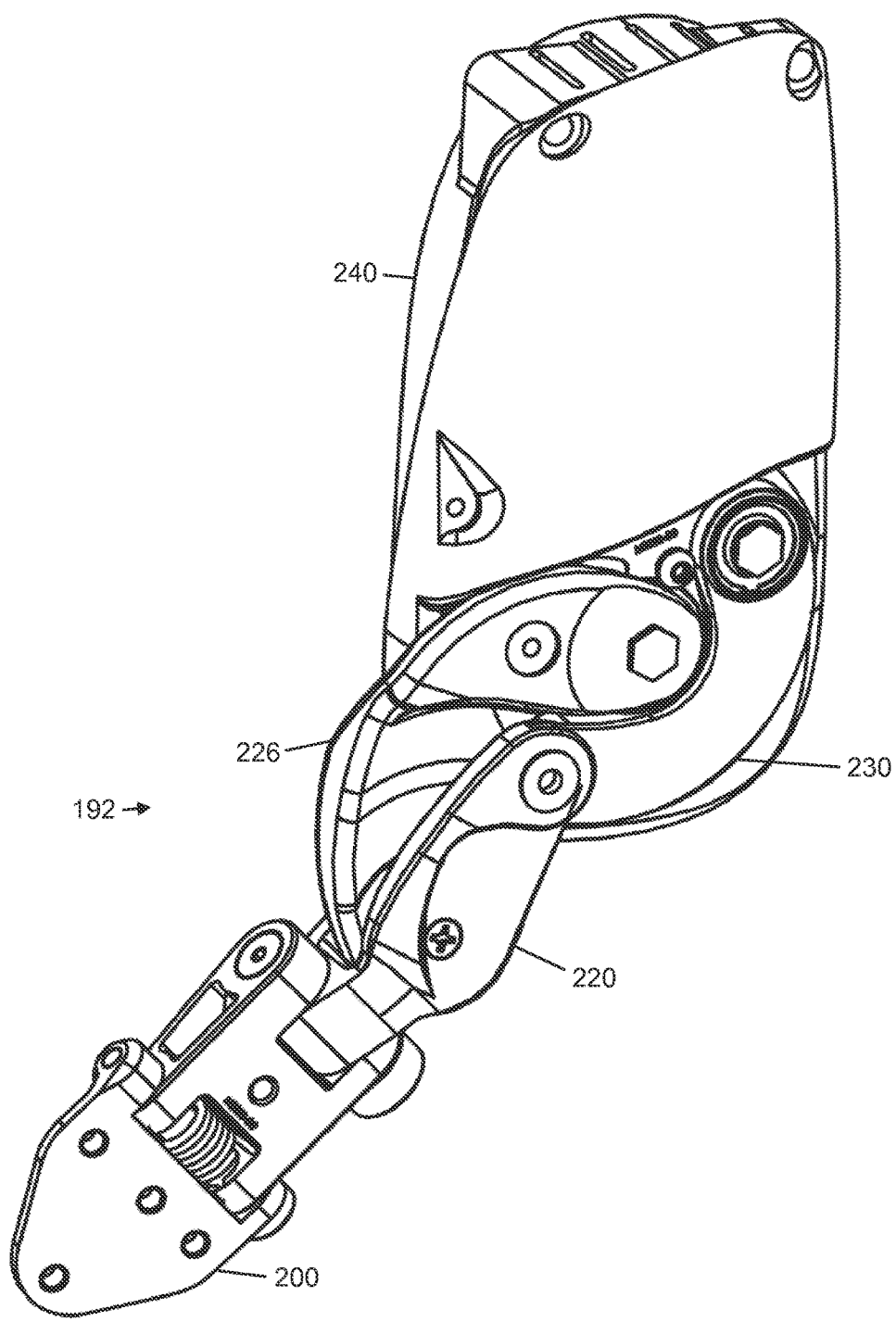
FIG. 19 is a three dimensional view of the four-bar linkage, with gearbox and lower connector.

FIG. 19 is a 3D view of the four-bar linkage 192 of FIGS. 13-15, showing the gearbox housing 240, the four-bar linkage and the mounting bracket 200. Tibia link 220, PCL link 226 and ACL link 230 are shown.

D. Variations

In other embodiments within the purview of the present invention, exemplary dimensions of the links of the four-bar linkage may be as follows. For example, the tibia link 220 may measure 40 mm from pivot 222 to pivot 224; the ACL link 230 may measure 70 mm from pivot 224 to pivot 232; the PCL link 226 may measure 81.5 mm from pivot 222 to pivot 228; and the femur link as defined by the gearbox housing 240 may measure 25 mm. As such the ratio of the links is given approximately by TIBIA:ACL:PCL:FEMUR=1.6:2.8:3.3:1. The pivots 222, 224 of the tibia link are aligned at an angle of 25° to the vertical, leaning forwards relative to the wearer. The pivots 228, 232 of the femur link are aligned at an angle of 20° to the vertical, leaning rearwards relative to the wearer.

If the distance between the pivots 228, 232 of the femur link is defined to be one unit whatever its actual measurement may be (for example, 1 unit is between about 21 mm and about 25 mm), then the distance between tibia pivots 222, 224 is between 1.3 and 1.6 units to one decimal place, the distance between ACL pivots 224, 232 is between 2.0 and 2.8 units to one decimal place; and the distance between PCL pivots 222, 228 is between 2.4 and 3.3 units to one decimal place.

In some embodiments, the condition (FEMUR+PCL)−(ACL+TIBIA)=0±0.1 units may be satisfied with a much closer tolerance to zero than ±0.1 units, such that (FEMUR+PCL) is substantially equal to (ACL+TIBIA). For example, the inter-pivot links may be: FEMUR=21.0 mm; PCL=50.0 mm; ACL=44.0 mm; and TIBIA=27.0 mm.

In general, unless otherwise indicated, singular elements may be in the plural and vice versa with no loss of generality. The use of the masculine can refer to masculine, feminine or both.

Throughout the description, specific details have been set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Although the present invention has been illustrated principally in relation to human knee joints, it may have application to other joints, e.g. those of animals.

It will be clear to one having skill in the art that variations to the specific details disclosed herein can be made, resulting in other embodiments that are within the scope of the invention disclosed. All parameters, dimensions, materials, ratios and configurations described herein are examples only and actual values of such depend on the specific embodiment. For example, angles, including, for example angles of mounting the tibia and femur links may be reasonably understood to be given to the nearest 5° in general. However, it is expected that alternate embodiments may be found if the angles were interpreted to be given to the nearest 10°. Accordingly, the scope of the invention is to be construed in accordance with the substance defined by the following claims.

The invention claimed is:

1. A four-bar linkage comprising:
a tibia link having first and second pivots;
a femur link having third and fourth pivots;

an ACL (anterior cruciate ligament) link connected to the first pivot and the third pivot; and
a PCL (posterior cruciate ligament) link crossed over the ACL link and connected to the second and fourth pivots;
wherein:
the distance between third and fourth pivots is one unit;
the distance between first and second pivots is between 1.3 and 1.6 units, to one decimal place;
the distance between first and third pivots is between 2.0 and 2.8 units, to one decimal place;
the distance between second and fourth pivots is between 2.4 and 3.3 units, to one decimal place; and
the sum of the distance between third and fourth pivots and the distance between second and fourth pivots is equal to the sum of the distance between first and third pivots and the distance between first and second pivots, to within a tolerance of 0.2 units.

2. The four-bar linkage of claim 1, included in a knee-mounted energy harvester, wherein a straight line between the first and second pivots is oriented leaning at a first angle of less than 45° forwards from a vertical direction when a wearer of the harvester is standing upright with extended knees.

3. The four-bar linkage of claim 2, wherein the first angle is between 10°±5° and 25°±5°.

4. The four-bar linkage of claim 3, wherein the first angle is 15°±5°.

5. The four-bar linkage of claim 1, included in a knee-mounted energy harvester, wherein a straight line between the third and fourth pivots is oriented leaning at a second angle of less than 45° rearwards from a vertical direction when a wearer of the harvester is standing upright with extended knees.

6. The four-bar linkage of claim 5, wherein the second angle is 20°±5°.

7. The four-bar linkage of claim 1, wherein the tibia link is connected to the ACL and PCL links via joints that permit the tibia link to twist about an axis between first and second pivots.

8. The four-bar linkage of claim 7, wherein the joints are spherical joints.

9. The four-bar linkage of claim 7, wherein the joints comprise elastomeric cups.

10. The four-bar linkage of claim 7, wherein:
the tibia link is connected via an articulated joint to a connector, which is connected via a further articulated joint to a shin brace;
the femur link is connected to a thigh brace; and
said articulated joints permit lateral movement of the shin brace relative to the thigh brace in a frame of reference of a wearer of said braces.

11. The four-bar linkage of claim 1, wherein the femur link is defined by a gearbox that converts relative angular motion, which occurs between the PCL link and the femur link, to electrical energy.

12. The four-bar linkage of claim 11, wherein an angular displacement of the femur link relative to the PCL link divided by an angular displacement of the femur link relative to the tibia link yields a leverage ratio that is steady to within about 20% over a range of 165° of angular displacement of the femur link relative to the tibia link.

13. The four-bar linkage of claim 11, wherein the tibia link, the ACL link and the PCL link have flat, curved shapes and an overlapping configuration such that pinch points between any two of said links are reduced over a range of 165° of angular displacement of the femur link relative to the tibia link, compared to if the tibia, ACL and PCL links had rectilinear shapes.

14. The four-bar linkage of claim 13, wherein:
the first and second pivots lie in a first plane that is different to a second plane in which the third and fourth pivots lie;
said pivots all have parallel axes; and
said distances are measured perpendicularly to said axes.

15. The four-bar linkage of claim 11, wherein angular displacement of the femur link relative to the tibia link is possible over a range from about −15° to about 200°, where 0° corresponds to an extended position of a knee joint.

16. The four-bar linkage of claim 1, wherein one unit is between about 21 mm and about 25 mm.

17. The four-bar linkage of claim 1, wherein the sum of the distance between third and fourth pivots and the distance between second and fourth pivots is equal to the sum of the distance between first and third pivots and the distance between first and second pivots, to within a tolerance of 0.1 units.

18. A four-bar linkage comprising:
a tibia link having first and second pivots;
a femur link having third and fourth pivots;
an ACL (anterior cruciate ligament) link connected to the first pivot and the third pivot; and
a PCL (posterior cruciate ligament) link crossed over the ACL link and connected to the second and fourth pivots;
wherein:
the distance between third and fourth pivots is one unit;
the distance between first and second pivots is between 1.3 and 1.4 units to one decimal place;
the distance between first and third pivots is between 2.0 and 2.1 units to one decimal place; and
the distance between second and fourth pivots is 2.4 units to one decimal place; and
the sum of the distance between third and fourth pivots and the distance between second and fourth pivots is equal to the sum of the distance between first and third pivots and the distance between first and second pivots, to within a tolerance of 0.1 units.

19. The four-bar linkage of claim 18, included in a knee-mounted energy harvester, wherein:
a straight line between the first and second pivots is oriented leaning at 15°±5° forwards from a vertical direction when a wearer of the harvester is standing upright with said knee extended;
a further straight line between the third and fourth pivots is oriented leaning at 20°±5° rearwards from said vertical direction;
the tibia link is connected to the ACL and PCL links via joints that permit the tibia link to twist about an axis between first and second pivots; and
an angular displacement of the femur link relative to the PCL link divided by an angular displacement of the femur link relative to the tibia link yields a leverage ratio that is steady to within about 20% over a range of about −15° to about 150° of flexion of said knee.

20. A four-bar linkage comprising:
a tibia link having first and second pivots;
a femur link having third and fourth pivots;
an ACL (anterior cruciate ligament) link connected to the first pivot and the third pivot; and
a PCL (posterior cruciate ligament) link crossed over the ACL link and connected to the second and fourth pivots;

wherein:

the distance between third and fourth pivots is one unit;

the distance between first and second pivots is between 1.3 and 1.4 units to one decimal place;

the distance between first and third pivots is between 2.0 and 2.1 units to one decimal place; and the distance between second and fourth pivots is 2.4 units to one decimal place; and the sum of the distance between third and fourth pivots and the distance between second and fourth pivots is substantially equal to the sum of the distance between first and third pivots and the distance between first and second pivots.

\* \* \* \* \*